(12) United States Patent
Rajasekaran et al.

(10) Patent No.: US 11,033,904 B2
(45) Date of Patent: Jun. 15, 2021

(54) METHODS, TOOLS, AND TOOL ASSEMBLIES FOR BIOMOLECULAR ANALYSIS USING MICROARRAYS

(71) Applicant: VIBRANT HOLDINGS, LLC, San Carlos, CA (US)

(72) Inventors: John J. Rajasekaran, Hillsborough, CA (US); Vasanth Jayaraman, San Mateo, CA (US); Tianhao Wang, San Mateo, CA (US); Kang Bei, San Mateo, CA (US); Hari Krishnan Krishnamurthy, San Mateo, CA (US); Karthik Krishna, Foster City, CA (US)

(73) Assignee: VIBRANT HOLDINGS, LLC, San Carlos, CA (US)

( * ) Notice: Subject to any disclaimer, the term of this patent is extended or adjusted under 35 U.S.C. 154(b) by 261 days.

(21) Appl. No.: 15/771,381

(22) PCT Filed: Oct. 25, 2016

(86) PCT No.: PCT/US2016/058589
§ 371 (c)(1),
(2) Date: Nov. 12, 2018

(87) PCT Pub. No.: WO2017/074900
PCT Pub. Date: May 4, 2017

(65) Prior Publication Data
US 2019/0030528 A1 Jan. 31, 2019

Related U.S. Application Data

(60) Provisional application No. 62/248,287, filed on Oct. 29, 2015.

(51) Int. Cl.
*B01L 3/00* (2006.01)
*C12Q 1/6837* (2018.01)
(Continued)

(52) U.S. Cl.
CPC ....... *B01L 3/50857* (2013.01); *B01L 3/50853* (2013.01); *C12Q 1/6837* (2013.01);
(Continued)

(58) Field of Classification Search
None
See application file for complete search history.

(56) References Cited

U.S. PATENT DOCUMENTS

| 5,244,788 A | 9/1993 | Hubscher |
| 6,182,719 B1 | 2/2001 | Yahiro |

(Continued)

FOREIGN PATENT DOCUMENTS

| DE | 4120139 A1 | 12/1992 |
| JP | H9-101302 A | 4/1997 |

(Continued)

OTHER PUBLICATIONS

PCT International Search Report and Written Opinion, PCT/US2016/058589, dated Dec. 23, 2016, 17 Pages.

(Continued)

*Primary Examiner* — Kathryn Wright
(74) *Attorney, Agent, or Firm* — Goodwin Procter LLP

(57) ABSTRACT

Disclosed herein are methods, tools, pillar plates, and tool assemblies for biomolecular analysis using microarrays that reduces the likelihood of air bubbles being trapped by the microarrays. Embodiments of the tools include two clamps that have a tool mount portion and a grasping portion. The tool mount portion is configured to engage a lifting mechanism of a plate handling robot for moving a pillar plate that include microarrays. The grasping portion is configured to freely suspend the pillar plate at an inclination of a non-zero tilt angle relative to a plane normal to the tool mount portion. Embodiments of pillar plates include two protruding edges on opposite sides of the pillar plate and a plurality of pillars (Continued)

with one or more affixed microarrays. Embodiments of the tool assembly include the tool and the pillar plate, wherein the protruding edges are configured to engage with the gasping portions.

24 Claims, 9 Drawing Sheets

(51) Int. Cl.
*G01N 1/28* (2006.01)
*G01N 35/00* (2006.01)
*G01N 35/02* (2006.01)

(52) U.S. Cl.
CPC ........... *G01N 1/28* (2013.01); *G01N 35/0099* (2013.01); *G01N 35/028* (2013.01); *B01J 2219/00317* (2013.01); *B01J 2219/00509* (2013.01); *B01L 2200/0647* (2013.01); *B01L 2200/0684* (2013.01); *B01L 2300/042* (2013.01); *B01L 2300/046* (2013.01); *B01L 2300/0819* (2013.01); *B01L 2300/0829* (2013.01); *G01N 2035/00158* (2013.01)

(56) References Cited

U.S. PATENT DOCUMENTS

| 8,652,774 | B2 | 2/2014 | Yamamoto et al. |
| 9,216,399 | B2 | 12/2015 | Rajasekaran et al. |
| 10,006,909 | B2 | 6/2018 | Rajasekaran et al. |
| 10,040,818 | B2 | 8/2018 | Jayaraman |
| 2003/0215360 | A1 | 11/2003 | Ruddock |
| 2006/0088863 | A1 | 4/2006 | Yamamoto et al. |
| 2006/0141612 | A1 | 6/2006 | Yamamoto et al. |
| 2006/0216207 | A1 | 9/2006 | Lehto |
| 2010/0030364 | A1 | 2/2010 | Fujimoto et al. |
| 2012/0309649 | A1 | 12/2012 | Lee et al. |
| 2015/0260712 | A1 | 9/2015 | Rajasekaran et al. |
| 2016/0144368 | A1 | 5/2016 | Isami et al. |
| 2016/0193608 | A1 | 7/2016 | Isami et al. |
| 2016/0288080 | A1 | 10/2016 | Rajasekaran et al. |
| 2017/0192007 | A1 | 7/2017 | Rajasekaran et al. |
| 2017/0269077 | A1 | 9/2017 | Rajasekaran et al. |
| 2018/0106795 | A1 | 4/2018 | Rajasekaran et al. |

FOREIGN PATENT DOCUMENTS

| JP | 2006-126204 A | 5/2006 |
| JP | 2015-158380 A | 9/2015 |
| WO | WO-2015/029691 A1 | 3/2015 |
| WO | WO 2017/117292 A1 | 7/2017 |

OTHER PUBLICATIONS

PCT International Preliminary Report on Patentability, PCT/US2016/058589, dated Mar. 16, 2018, 30 Pages.

U.S. Appl. No. 15/991,706, filed May 29, 2018, inventor: John J. Rajasekaran, [copy not enclosed].

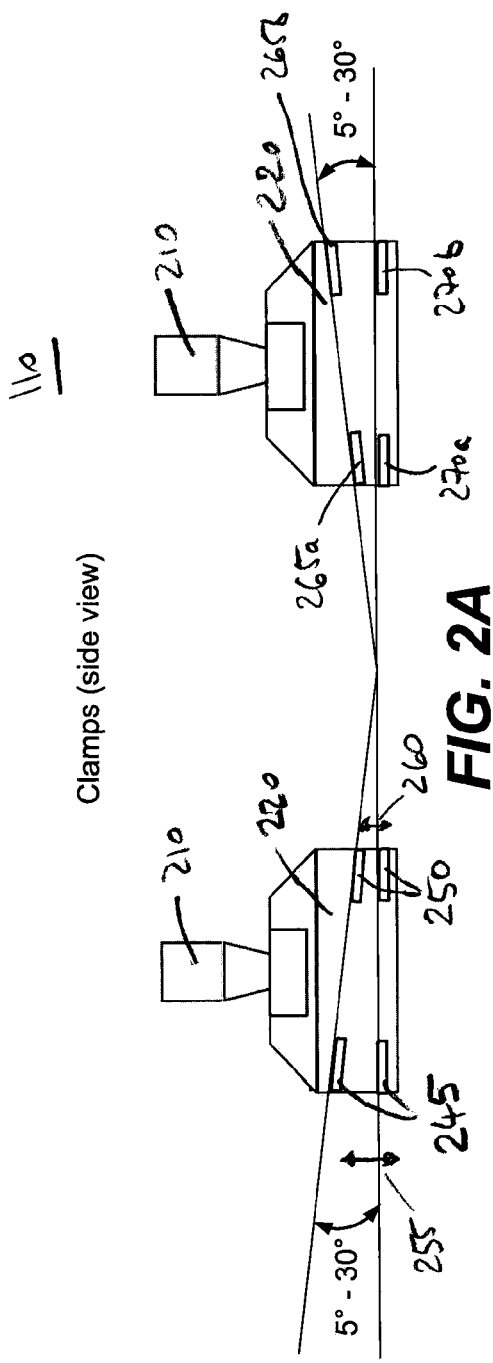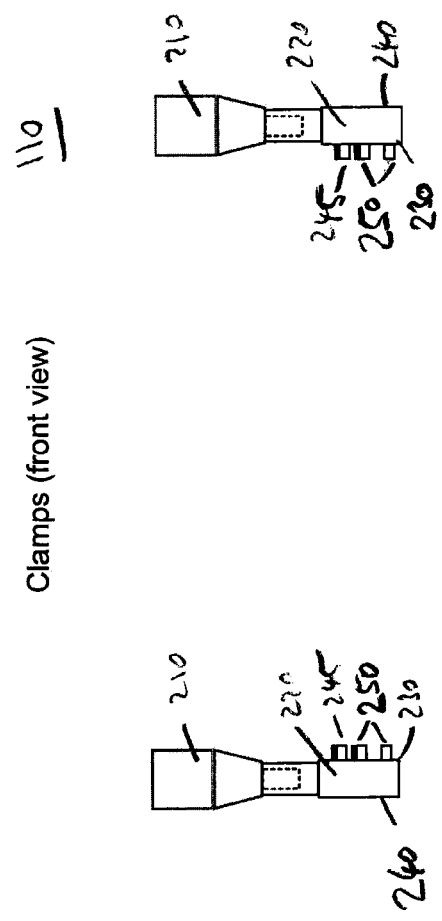

METHODS, TOOLS, AND TOOL ASSEMBLIES FOR BIOMOLECULAR ANALYSIS USING MICROARRAYS

CROSS REFERENCE TO RELATED APPLICATIONS

This application is the National Stage of International Application No. PCT/US2016/058589, filed Oct. 25, 2016, which claims the benefit of U.S. Provisional Application No. 62/248,287, filed Oct. 29, 2015, which are hereby incorporated in their entirety by reference.

BACKGROUND

A typical microarray system is generally comprised of biomolecular probes, such as DNA, proteins, or peptides, formatted on a solid planar surface like glass, plastic, or silicon chip, plus the instruments needed to handle samples (automated robotics), to read the reporter molecules (scanners) and analyze the data (bioinformatic tools). Microarray technology can facilitate monitoring of many probes per square centimeter. Advantages of using multiple probes include, but are not limited to, speed, adaptability, comprehensiveness and the relatively cheaper cost of high volume manufacturing. The uses of such microarray include, but are not limited to, diagnostic microbiology, including the detection and identification of pathogens, investigation of antimicrobial resistance, epidemiological strain typing, investigation of oncogenes, analysis of microbial infections using host genomic expression, and polymorphism profiles.

In a system that uses microarrays for biomolecular analysis the microarrays are functionalized with distinct analyte-detecting regions or probes that are synthesized on a substrate of the microarrays by techniques well known to one skilled in the art, e.g., chemo selective immobilization or solid phase synthesis. Multiple functionalized microarrays are typically placed on plates for parallel assaying the microarrays. In some case, the microarrays with the biomolecular probes are affixed to inverted pillar plates for more efficient handling and assaying the probes. The pillar or immersion plates are referred to as "inverted," if the surface of the pillar, on which the microarrays are affixed, faces downwards when assaying the probes on the microarrays.

To assay the probes, the microarrays are typically immersed in assay solution contained in wells on a well plate. A plate handling system vertically moves the plate with the microarrays towards a well plate having corresponding wells for each pillar. Moving the pillar plate and well plate close enough results in the flat microarrays contacting the surfaces of the assay solution. By further moving the two plates together, the microarrays immerse into the assay solution. Oftentimes, air bubbles in the solution are generated and trapped close to the microarrays when the microarrays are immersed in the solution. These air bubbles negatively affect the results from analyzing the assay, since the bubbles, for example, prevent the solution to fully contact all the probes, leaving some probes surrounded by air instead of assay solution. Thus, while using inverted pillar plates in microarray systems allows for efficient handling and assaying of large number of probes in terms of speed, adaptability, cost and comprehensiveness of the biomolecular analysis, the generation of air bubbles in these systems present a significant disadvantage in reliability and accuracy of these systems.

SUMMARY

The present disclosure includes methods, tools, pillar plates, and tool assemblies for assaying microarrays that reduces the likelihood of air bubbles being trapped by the microarrays.

In some embodiments, the tools include two clamps with each clamps including: (1) a tool mount portion that is configured to engage a lifting mechanism of a plate handling robot for moving a pillar plate comprising microarrays; (2) and a grasping portion that is configured to freely suspend a pillar plate at an inclination of a non-zero tilt angle relative to a plane normal to the tool mount portion. Although the disclosure generally refers to pillar plates, the term "pillar plate" also includes plates that lack pillars. In some embodiments, the non-zero tilt angle is 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, or 30°. In some embodiments, the non-zero tilt angle is within the range of 5° to 30°, less or equal to 30°, or less or equal to 45°.

In some embodiments, the pillar plate is freely suspended with pillars of the pillar plate facing downwards and one or more microarrays being affixed to at least one pillar. In some embodiments, a pillar plate includes to an inverted pillar plate. In some of these embodiments, the one or more microarrays are affixed directly to the plate and not to at least one pillar. In some embodiments, the microarrays are functionalized with distinct analyte-detecting regions or biomolecular probes that are synthesized on a substrate of the microarrays by well-known techniques, e.g., the synthesis described in more detail below.

The one or more microarrays are immersed in assay solution by using the tools and tool assemblies to move the pillar plate towards a well plate including wells that are configured to hold assay solution. In some embodiments, each pillar is received by a corresponding well of the well plate prior to the pillar contacting an assay solution in the well.

In some embodiments, the grasping portion of each clamp of the tool includes two pairs of receiving bars. The receiving bars of the first pair are separated at a first vertical width and the receiving bars of the second pair are separated at a second vertical width. In some embodiments, the first vertical width exceeds the second vertical width by a predefined threshold distance whereby the pillar plate assumes the non-zero tilt angle if the pillar plate is freely suspended by the two clamps.

The advantage of having the pillar plate at a non-zero tilt angle is the reduced likelihood of generating air bubbles in the assay solution when the microarrays are immersed in the solution. Less to no air bubbles are generated, since the edge and not the flat surface of the pillars first pierces the surface of the assay solution when the pillar contacts and immerses into the solution. With a smaller total area of the pillar edge as compared planar top surface of the pillars, the energy to overcome the surface tension of the assay solution is significantly reduces, decreasing the number of bubbles generated. Furthermore, since the pillar immerses at a tilt angle, generated bubbles can percolate along the tilted pillar surface towards the surface of the solution without being trapped underneath the pillar.

In some embodiments, the pillar plate include a plurality of pillars that extend approximately perpendicular from the pillar plate with one or more microarrays being affixed to at least one pillar so that each microarray is prevented from being displaced from the at least one pillar when the pillar plate is turned upside down. The pillar plate further includes two protruding edges on opposite sides of the pillar plate, wherein the protruding edges are configured to engage with grasping portions of clamps of the tool.

In some embodiments, the tool assemblies include the tool and a pillar plate. The pillar plate includes a plurality of pillars that extend approximately perpendicular from the pillar plate. One or more microarrays are affixed to at least one pillar so that each microarray is prevented from being displaced from the at least one pillar when the pillar plate is turned upside down. The pillar plate further includes two protruding edges on opposite sides of the pillar plate, which are configured to engage with the grasping portions of the clamps to suspend the pillar plate. In some embodiments, each of two protruding edges are both separately interlocked with the two pairs of receiving bars of one of the two clamps if the pillar plate is suspended by the two clamps.

In some embodiments, the methods include a method of using a tool assembly for assaying microarrays that reduces the likelihood of air bubbles being trapped by the microarrays. The method includes providing the tool assembly and providing a well plate comprising a plurality of well. Each well in the method is capable of receiving one pillar of the pillar plate, when the pillar plate is inclined at the non-zero tilt angle relative to the plane normal to the tool mount portion of the clamps and the microarrays are contacted with an assay solution in one or more wells of the well plate. The method further includes freely suspending the pillar plate of the tool assembly inclined at the non-zero tilt angle relative to the plane normal to the tool mount portion of the clamps. The step of freely suspending includes interlocking the protruding edges of the pillar plate with the grasping portions of the clamps, while the pillar plate is turned upside down and the tool mount portion of the clamps are engaged with a lifting mechanism of a plate handling robot. In the method, the one or more microarrays affixed to the at least one pillar of the pillar plate are assayed by moving the freely suspended pillar plate towards the well plate and contacting the one or more microarray with an assay solution in the wells.

BRIEF DESCRIPTION OF THE SEVERAL VIEWS OF THE DRAWINGS

These and other features, embodiments, and advantages of the present invention will become better understood with regard to the following description, and accompanying drawings, where:

FIGS. 2A and 2B illustrates a side view and a top view of a tool including the two clamps for assaying microassay, respectively, according to some embodiments.

Figure 1:
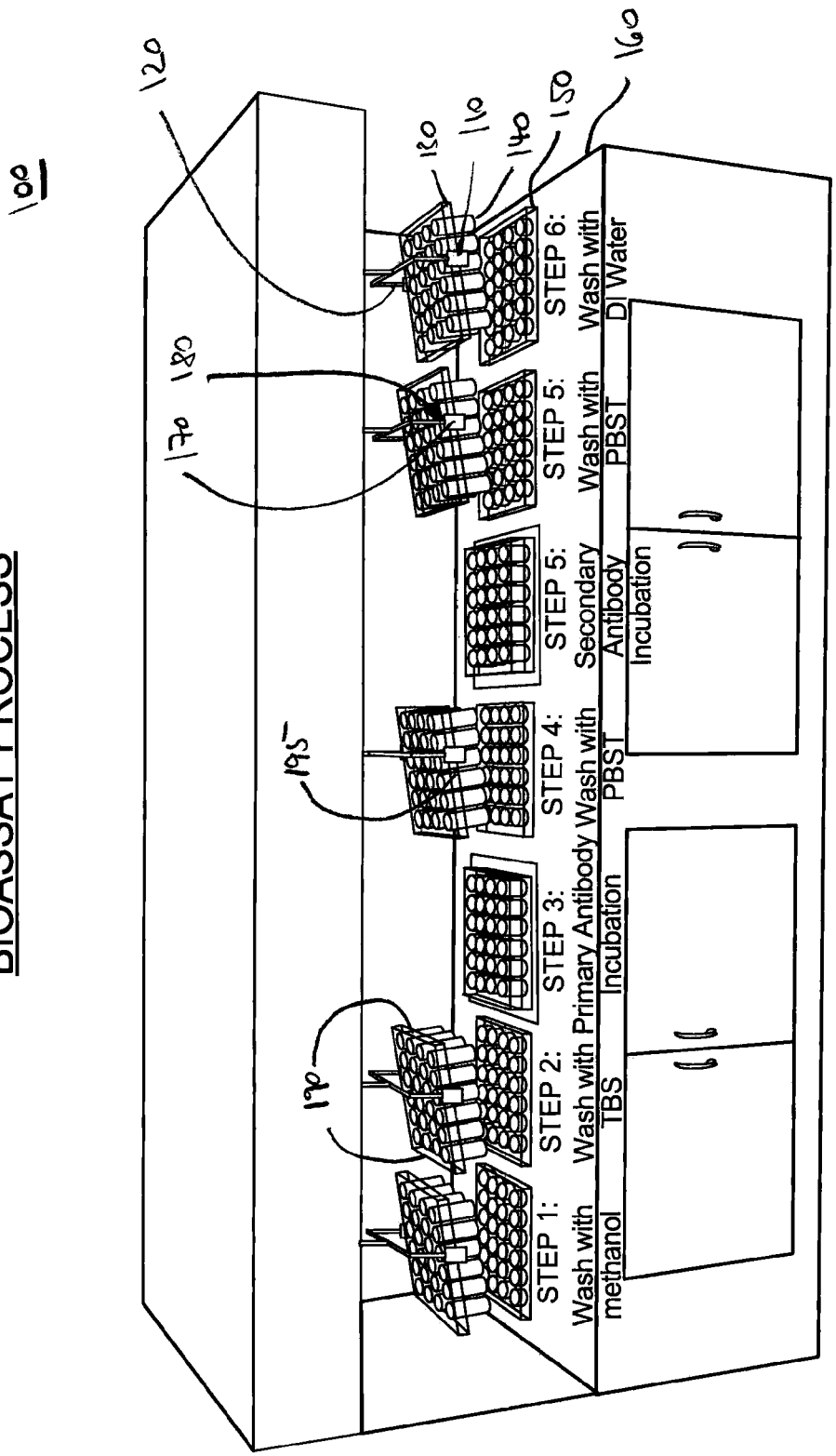
FIG. 1 illustrates a workbench system for performing steps in an assay using tools and tool assemblies, according to some embodiments.

It should be understood based on the present disclosure that the pillar plates illustrated in the figures can have microarrays affixed to the pillar plates, for example, to a top surface of the pillars of the pillar plates, although these microarrays are not explicitly shown in the figures.

DETAILED DESCRIPTION

The present disclosure describes methods, tools, pillar plates, and tool assemblies for assaying microarrays that reduces the likelihood of air bubbles being trapped by the microarrays. The tools and tool assemblies for assaying microarrays include several novel configurations of clamps and pillar plates with microarrays affixed to the plates. The tools and tool assemblies allow moving pillar plates at a non-zero tilt angle relative to a mount portion of the tools. Some embodiments relates to inverted pillar plates including a plurality of pillars with one or more microarray affixed to at least one of the pillars and the pillars facing downwards. In some embodiments, the microarrays are functionalized with distinct analyte-detecting regions or biomolecular probes that are synthesized on a substrate of the microarrays by well-known techniques, e.g., the synthesis described in more detail below.

The non-zero tilt angle reduces the likelihood of generating and subsequently trapping air bubbles by the microarrays, when the microarrays are immersed in an assay solution. The tools and tool assemblies of the present disclosure may be used once or may be used multiple times. In some embodiments, the tools and tool assemblies (e.g., clamps and plates) are disposable.

Definitions

Terms used in the claims and specification are defined as set forth below unless otherwise specified.

As used herein the term "wafer" refers to a slice of semiconductor material, such as a silicon or a germanium crystal generally used in the fabrication of integrated circuits. Wafers can be in a variety of sizes from, e.g., 25.4 mm (1 inch) to 300 mm (11.8 inches) along one dimension with thickness from, e.g., 275 µm to 775 µm.

As used herein the term "photoresist" or "resist" or "photoactive material" refers to a light-sensitive material that changes its solubility in a solution when exposed to ultra violet or deep ultra violet radiation. Photoresists are organic or inorganic compounds that are typically divided into two types: positive resists and negative resists. A positive resist is a type of photoresist in which the portion of the photoresist that is exposed to light becomes soluble to the photoresist developer. The portion of the photoresist that is unexposed remains insoluble to the photoresist developer. A negative resist is a type of photoresist in which the portion of the photoresist that is exposed to light becomes insoluble to the photoresist developer. The unexposed portion of the photoresist is dissolved by the photoresist developer.

As used herein the term "photomask" or "reticle" or "mask" refers to an opaque plate with transparent patterns or holes that allow light to pass through. In a typical exposing process, the pattern on a photomask is transferred onto a photoresist.

As used herein the term "coupling molecule" includes in one embodiment any natural or artificially synthesized amino acid with its amino group protected with a fluorenylmethyloxycarbonyl (Fmoc) or tert-Butyloxycarbonyl (boc) group. These amino acids may optionally have their side chains protected. Examples of coupling molecules include, but are not limited to, boc-Gly-COOH, Fmoc-Trp-COOH. Other embodiments of coupling molecules include monomer molecules and combinations thereof that can form polymers upon coupling, e.g., nucleotides, sugars and the like, and are described below.

As used here in the term "coupling" or "coupling process" or "coupling step" refers to a process of forming a bond between two or more molecules such as a linker molecule or a coupling molecule. A bond can be a covalent bond such as a peptide bond. A peptide bond can a chemical bond formed between two molecules when the carboxyl group of one coupling molecule reacts with the amino group of the other coupling molecule, releasing a molecule of water ($H_2O$). This is a dehydration synthesis reaction (also known as a condensation reaction), and usually occurs between amino acids. The resulting —C(═O)NH— bond is called a peptide bond, and the resulting molecule is an amide.

As used herein the terms "polypeptide," "peptide," or "protein" are used interchangeably to describe a chain or polymer of amino acids that are linked together by bonds. Accordingly, the term "peptide" as used herein includes a dipeptide, tripeptide, oligopeptide, and polypeptide. The term "peptide" is not limited to any particular number of amino acids. In some embodiments, a peptide contains about 2 to about 50 amino acids, about 5 to about 40 amino acids, or about 5 to about 20 amino acids. A molecule, such as a protein or polypeptide, including an enzyme, can be a "native" or "wild-type" molecule, meaning that it occurs naturally in nature; or it may be a "mutant," "variant," "derivative," or "modification," meaning that it has been made, altered, derived, or is in some way different or changed from a native molecule or from another molecule such as a mutant. A "point mutation" refers to the mutation of one amino acid among the amino acids in a sequence of a peptide.

As used herein the term "biomarkers" includes, but is not limited to DNA, RNA, proteins (e.g., enzymes such as kinases), peptides, sugars, salts, fats, lipids, ions and the like.

As used herein the term "linker molecule" or "spacer molecule" includes any molecule that does not add any functionality to the resulting peptide but spaces and extends out the peptide from the substrate, thus increasing the distance between the substrate surface and the growing peptide. This generally reduces steric hindrance with the substrate for reactions involving the peptide (including uni-molecular folding reactions and multi-molecular binding reactions) and so improves performance of assays measuring one or more embodiments of peptide functionality.

As used herein the term "developer" refers to a solution that can selectively dissolve the materials that are either exposed or not exposed to light. Typically developers are water-based solutions with minute quantities of a base added. Examples include tetramethyl ammonium hydroxide in water-based developers. Developers are used for the initial pattern definition where a commercial photoresist is used.

As used herein the term "protecting group" includes a group that is introduced into a molecule by chemical modification of a functional group in order to obtain chemoselectivity in a subsequent chemical reaction. "Chemoselectivity" refers to directing a chemical reaction along a desired path to obtain a pre-selected product as compared to another. For example, the use of boc as a protecting group enables chemoselectivity for peptide synthesis using a light mask and a photoacid generator to selectively remove the protecting group and direct pre-determined peptide coupling reactions to occur at locations defined by the light mask.

As used herein the term "microarray," "array" or "chip" refers to a substrate on which a plurality of probe molecules of protein or specific DNA binding sequences have been affixed at separate locations in an ordered manner thus forming a microscopic array. Protein or specific DNA binding sequences may be bound to the substrate of the chip through one or more different types of linker molecules. A "chip array" refers to a plate having a plurality of chips, for example, 24, 96, or 384 chips.

As used herein the term "probe molecules" refers to, but is not limited to, proteins, DNA binding sequences, antibodies, peptides, oligonucleotides, nucleic acids, peptide nucleic acids ("PNA"), deoxyribonucleic acids (DNA), ribonucleic acids (RNA), peptide mimetics, nucleotide mimetics, chelates, biomarkers and the like. As used herein, the term "feature" refers to a particular probe molecule that has been attached to a microarray. As used herein, the term "ligand" refers to a molecule, agent, analyte or compound of interest that can bind to one or more features.

As used herein the term "microarray system" or a "chip array system" refers to a system usually comprised of probe molecules formatted on a solid planar surface like glass, plastic or silicon chip plus the instruments needed to handle samples (automated robotics), to read the reporter molecules (scanners) and analyze the data (bioinformatic tools).

As used herein the term "patterned region" or "pattern" or "location" refers to a region on the substrate on which are grown different features. These patterns can be defined using photomasks.

As used herein the term "derivatization" refers to the process of chemically modifying a surface to make it suitable for bio molecular synthesis. Typically derivatization includes the following steps: making the substrate hydrophilic, adding an amino silane group, and attaching a linker molecule.

As used herein the term "capping" or "capping process" or "capping step" refers to the addition of a molecule that prevents the further reaction of the molecule to which it is attached. For example, to prevent the further formation of a peptide bond, the amino groups are typically capped by acetylation in the presence of an acetic anhydride molecule.

As used herein the term "diffusion" refers to the spread of, e.g., photoacid through random motion from regions of higher concentration to regions of lower concentration.

As used herein the term "dye molecule" refers to a dye which typically is a colored substance that can bind to a substrate. Dye molecules can be useful in detecting binding between a feature on an array and a ligand, e.g. a molecule of interest.

As used herein, the terms "immunological binding" and "immunological binding properties" refer to the non-covalent interactions of the type which occur between an immunoglobulin molecule and an antigen for which the immunoglobulin is specific.

As used herein the term "biological sample" refers to a sample derived from biological tissue or fluid that can be assayed for an analyte(s) of interest or any ligand. Such samples include, but are not limited to, sputum, amniotic fluid, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Although the sample is typically taken from a human patient, the assays can be used to detect analyte(s) of interest in samples from any organism (e.g., mammal, bacteria, virus, algae, or yeast) or mammal, such as dogs, cats, sheep, cattle, and pigs. The sample may be pretreated as necessary by dilution in an appropriate buffer solution or concentrated, if desired.

As used herein, the term "assay" refers to a type of biochemical test that measures the presence or concentration of a substance of interest in solutions that can contain a complex mixture of substances.

The term "antigen" as used herein refers to a molecule that triggers an immune response by the immune system of a subject, e.g., the production of an antibody by the immune system. Antigens can be exogenous, endogenous or auto antigens. Exogenous antigens are those that have entered the body from outside through inhalation, ingestion or injection. Endogenous antigens are those that have been generated within previously-normal cells as a result of normal cell metabolism, or because of viral or intracellular bacterial infection. Auto antigens are those that are normal protein or protein complex present in the host body but can stimulate an immune response.

As used herein the term "epitope" or "immunoactive regions" refers to distinct molecular surface features of an antigen capable of being bound by component of the adaptive immune system, e.g., an antibody or T cell receptor. Antigenic molecules can present several surface features that can act as points of interaction for specific antibodies. Any such distinct molecular feature can constitute an epitope. Therefore, antigens have the potential to be bound by several distinct antibodies, each of which is specific to a particular epitope.

As used herein the term "antibody" or "immunoglobulin molecule" refers to a molecule naturally secreted by a particular type of cells of the immune system: B cells. There are five different, naturally occurring isotypes of antibodies, namely: IgA, IgM, IgG, IgD, and IgE.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

It must be noted that, as used in the specification and the appended claims, the singular forms "a," "an," and "the" include plural referents unless the context clearly dictates otherwise.

Compositions

Tools for Assaying Microarrays

In some embodiments, the tools for assaying microarrays include two clamps with each clamps including: (1) a tool mount portion that is configured to engage a lifting mechanism of a plate handling robot for moving a pillar plate comprising microarrays; (2) and a grasping portion that is configured to freely suspend a pillar plate at an inclination of a non-zero tilt angle relative to a plane normal to the tool mount portion. In some embodiments, the non-zero tilt angle is 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, or 30°. In some embodiments, the non-zero tilt angle is within the range of 5° to 30°, less or equal to 30°, or less or equal to 45°.

In some embodiments, the microarrays are functionalized with distinct analyte-detecting regions or biomolecular probes that are synthesized on a substrate of the microarrays by well-known techniques, e.g., the synthesis described in more detail below. In some embodiments, one or more microarray is affixed to at least one pillar of the pillar plate so that to prevent displacement of the microarray form the at least one pillar when the pillar plate is turned upside down during assaying biomolecular probes on the microarray. In some embodiments, microarrays are affixed to a top surface of the pillars with an adhesive. In some embodiments, the adhesive is an epoxy, a visible light curable epoxy, an ultraviolet light curable glue, or a heat curable glue epoxy.

The tools may be used in a robotic plate system that handles the pillar plate and performs the steps of assaying the microarrays. In some embodiments, the tools are used in combination with various assay modules (e.g., plates, dipsticks, measurement cells, cassettes, cartridges, elements or devices), plates or module components, and apparatuses for performing luminescence-based assays.

Robotic Plate System

FIG. 1 illustrates the tools and tool assembly as part of a robotic plate system, according to some embodiments. The robotic plate system 100 includes clamps 110, clamp arms 120 coupled to a lifting mechanism, pillar plates 130 with one or more microarrays attached to at least one pillar 140, and well plates 150 that are placed on a workbench 160 and include various assay solutions. The illustrated assay process of the pillar plates included the following six steps: placing and washing the pillar plate in a first well plate filled methanol, picking up the pillar plate from the first well plate and transporting it to a second well plate filled with TBS for washing. In the third step, the process places the pillar plate in third well plate for incubation with the primary antibody, followed by washing the pillar plate in a fourth well plate containing PBST. The next step includes placing the pillar plate in a fifth well plate for incubation with the secondary antibody, followed by washing the pillar plate in a sixth well plate with PBST and then by washing it in a seventh well plate with DI water before drying the pillar plate in nitrogen for further analysis.

Between each assay step, using the clamps 110 and clamp arms 120 coupled to the lifting mechanism a plate handling robot of the system 100 moves the pillar plate 130 from one well plate 150 to a neighboring well plate 150 on the workbench 160. As illustrated in FIG. 1, the grasping portion of the clamps 110 engage the pillar plates 130 at a position 170 that is off-center along the side of the plate relative to the pillar plates when moving the pillar plates along the workbench 160. Engaging at the off-center position 170 results in a non-zero angle inclination of the pillar plates 130 relative to the tool mount portion 180 of the clamps 110 due to the imbalance of the gravitational forces pulling on each end 190 of the pillar plates. In some embodiments, the off-center position is closer to the end of the pillar plate that is facing the direction in which the pillar plate is moved by the robotic plate system. In some embodiments, the off-center position is closer to the end of the pillar plate that is opposite to the direction in which the pillar plate is moved by the robotic plate system. Based on the off-center position, the non-zero tilt angle increases or decreases as the off-center position is located farther or closer to the center of the pillar plate, respectively.

As illustrated in FIG. 1, the tools allow lifting and moving the pillar plate 130 at a non-zero tilt angle relative to the mount portion 170 of the clamps 110 between assaying the microarrays. In some embodiments, the robotic plate system 100 includes a liquid handling assay station that is automated to perform liquid handling for providing assay solutions to the well plates and assaying the microarrays. In some embodiments, the liquid handling assay station is any commercially available one that can use the standard or custom-made well plates.

After performing assays using the robotic plate system 100, the one or more microarray is scanned using any commercially available confocal, CCD, sCMOS or CMOS scanner. In some embodiments, the scanner scans multiple microarrays. In some embodiments, the data from the scanner is analyzed on a Vibrant Bio Analyzer.

In some embodiments, one or several autoloader units feed the pillar plates 130 to the robotic plate system 100. In some embodiments, one or several autoloader units place the well plates 150 on the workbench 160. In some embodiments, the microarrays are scanned on the scanner using an autoloader. In some embodiments, one or several scanners are connected to the autoloader to allow the autoloader to transfer the pillar plates 130 with the assayed microarrays to a one or a plurality of scanners.

In some embodiments, the tools are used for scanning the microarrays affixed to the pillar plate. In some embodiments, the grasping portion of the clamps 110 engages the pillar plates 130 at a position that is at the center 195 along the side relative to the pillar plates. To scan the microarrays the pillar of the plates are facing upwards when moving the pillar plate underneath the scanner. Engaging the at center position results in a zero angle inclination of the pillar plates relative to the tool mount portion 180 of the clamps 110. In this case, the gravitational forces pulling on each end 190 of the pillar plates balance each other out.

Clamps

FIGS. 2A and 2B illustrates a side view and a top view of the two clamps 110, respectively, according to some embodiments. Each clamp 110 includes a tool mount portion 210 and a grasping portion 220. The tool mount portion is configured to engage a lifting mechanism of robotic plate system through clamps arm for moving the pillar plates. The grasping portion 220 is configured to freely suspend a pillar plate at an inclination of a non-zero tilt angle relative to a plane normal to the tool mount portion 210.

In some embodiments, the non-zero tilt angle is 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, or 30°. In some embodiments, the non-zero tilt angle is within the range of 5° to 30° (as illustrated in FIG. 2A), less or equal to 30°, or less or equal to 45°.

In some embodiments, the grasping portion 220 includes an inner surface 230 and an outer surface 240. The inner surface 230 facing towards and contacting the pillar plate when the clamps of the tool engages with the pillar plate to suspend and move the pillar plate. In some embodiments, the grasping portion of each clamp includes two pairs of receiving bars 245 and 250. The receiving bars 245 of the first pair being separated at a first vertical width 255, while the receiving bars 250 of the second pair are separated at a second vertical width 260. Thus, each pair of receiving bars forms a separate throat having different width for receiving a protruding edge of the pillar plate.

In some embodiments, the first vertical width exceeds the second vertical width by a pre-defined threshold distance whereby the pillar plate assumes the non-zero tilt angle if the pillar plate is freely suspended by the two clamps of the tool. In some embodiments, the pre-defined threshold distance equals a factor times the first vertical width with the factor falls within the range of 1 to 2. In some embodiments, the first vertical width is 2.75 mm. In some embodiments, the first vertical width is less than 5 mm. In some embodiments, the first vertical width falls within the range of 1 mm to 5 mm. In some embodiments, the first vertical width is 1 mm, 1.5 mm, 2 mm, 2.5 mm, 3 mm, 3.5 mm, 4 mm, 4.5 mm, or 5 mm. In some embodiments, the first vertical width is larger than 5 mm. In some embodiments, the second vertical width is less than 5.5 mm. In some embodiments, the second vertical width is larger than 5.5 mm.

In some embodiments, as illustrated in FIG. 2A, the upper receiving bars 265a, 265b of the two pairs are aligned at the non-zero tilted angle and the lower receiving bars 270a, 270b are aligned parallel relative to a plane normal to the tool mount portion. In some embodiments, the clamps include more than two pairs of receiving bars. In some embodiments, the receiving bars of the two pairs are connected to form a single pair of receiving bars.

In some embodiments, the receiving bars 245, 250 extend perpendicular from the inner surface 230 of the clamps. In some embodiments, the receiving bars extend a distance that falls within the range of 0.5 mm to 5 mm from the inner surface of the grasping portion. In some embodiments, the receiving bars extend 1 mm from the inner surface. In some embodiments, the receiving bars extend less than 5 mm from the inner surface of the edges of the receiving bar. In some embodiments, the receiving bars extends more than 0.5 mm from the inner surface. In some embodiments, the edges of the receiving bars are graded or rounded to facilitate receiving the protruding edges of the pillar plates.

In some embodiments, the grasping portions of the two clamps are configured to allow a planar surface of the pillar plate to align parallel relative to the plane normal to the tool mount portion if the pillar plate is not freely suspended by the two clamps and is instead buoyant by an assay solution in the one or more wells of a well plate. For example, the lower receiving bars 270a, 270b are arranged on the inner surface in a linear alignment perpendicular to the tool mount portion 210.

Pillar Plates

Figure 3A:
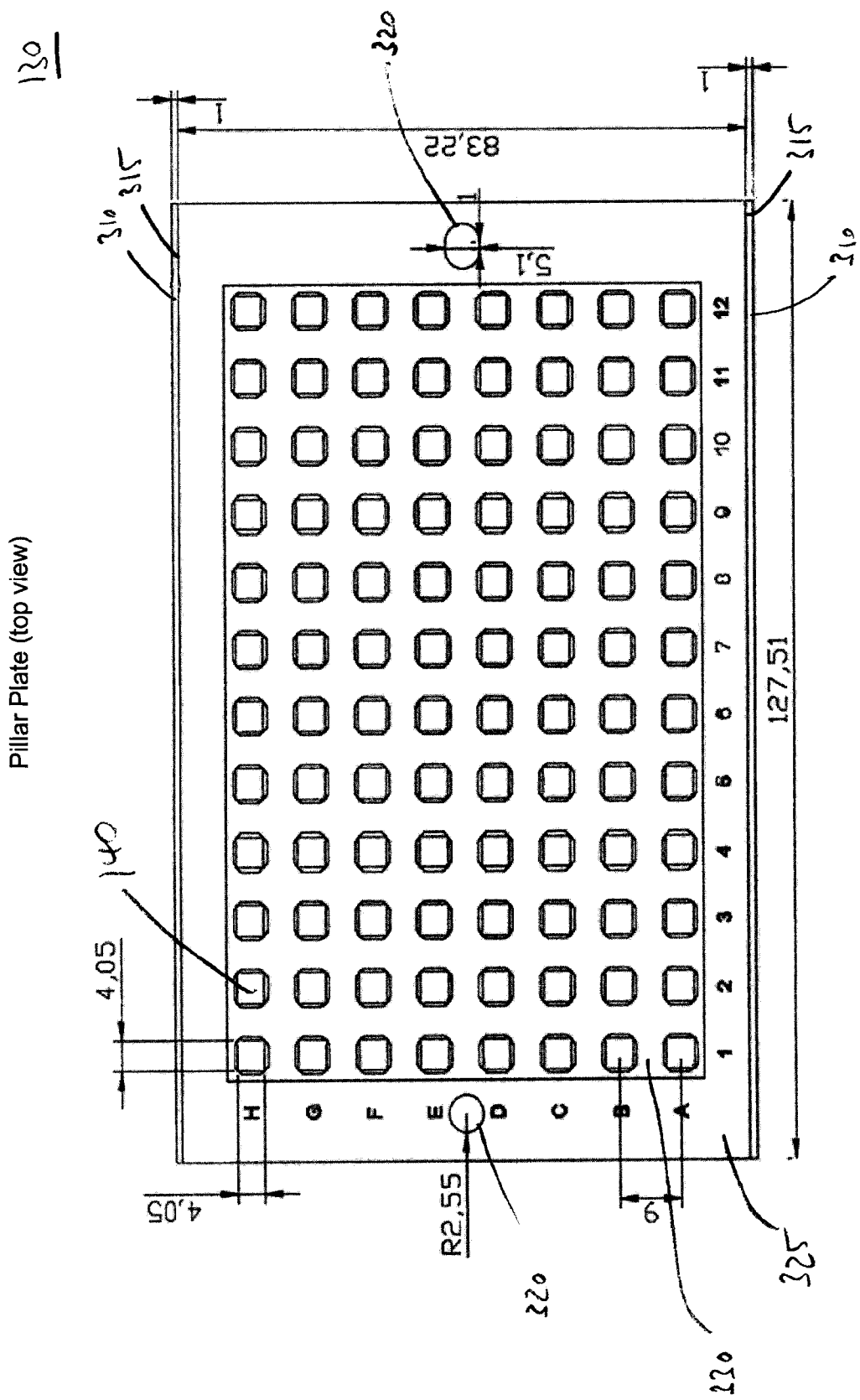
FIGS. 3A-3D illustrates pillar plates used for assaying microarrays, including the dimensions of a 24-pillar and 96-pillar plate, respectively, according to some embodiments.

FIGS. 3A-3D illustrate pillar plates for assaying microarrays, according to some embodiments. FIG. 3A shows a top view of an embodiment of a 96-pillar plate 130, including the dimensions of the plate in mm. In some embodiments, the pillar plate 130 includes two protruding edges 310 on the opposite sides 315 of the pillar plate 130. The protruding edges are configured to engage with the grasping portions of the clamps to suspend the pillar plate.

In some embodiments, the pillar plate 130 further includes one or more alignment marks 320, a plate support 325, and a base region 330 on mounting the pillars 335. In some embodiments, the alignment marks 320 are centered on each side of the plate support 325 as shown in FIG. 3A. In some embodiments, the alignment marks 320 are placed at opposite corners of the plate support 325 as shown in FIGS. 3C and 3D. In some embodiments, the pillars 140 are cylindrical shape as shown in FIGS. 3C and 3D. In the embodiment shown in FIG. 3A, the pillars have a rectangular shape with the graded edges. Other embodiments include various shapes and sizes of pillars that are known to a person skilled in the art. In some embodiments, the pillar plate has an area that is larger than 50 square centimeters.

Figure 3B:
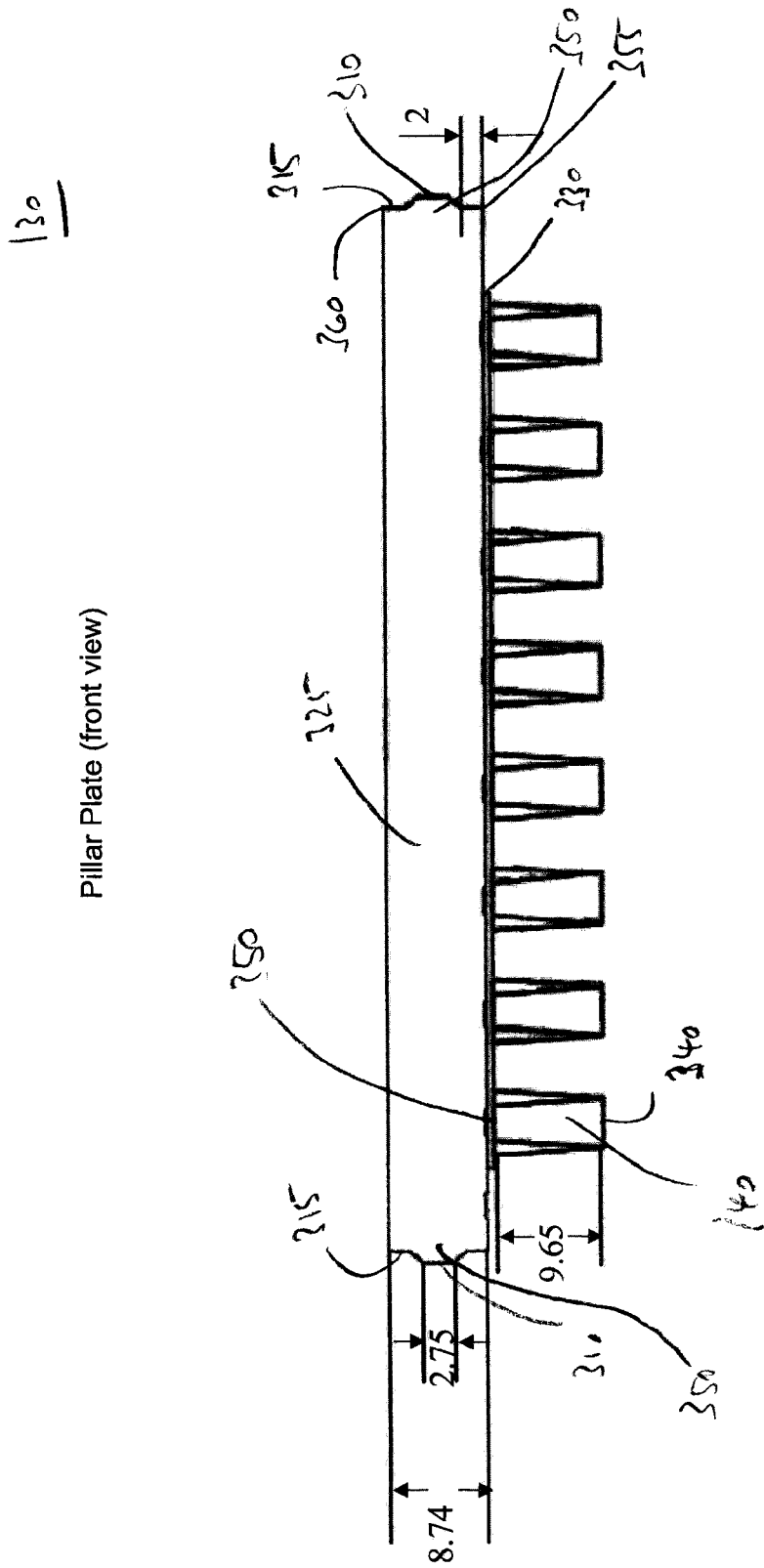
Figure 3C:
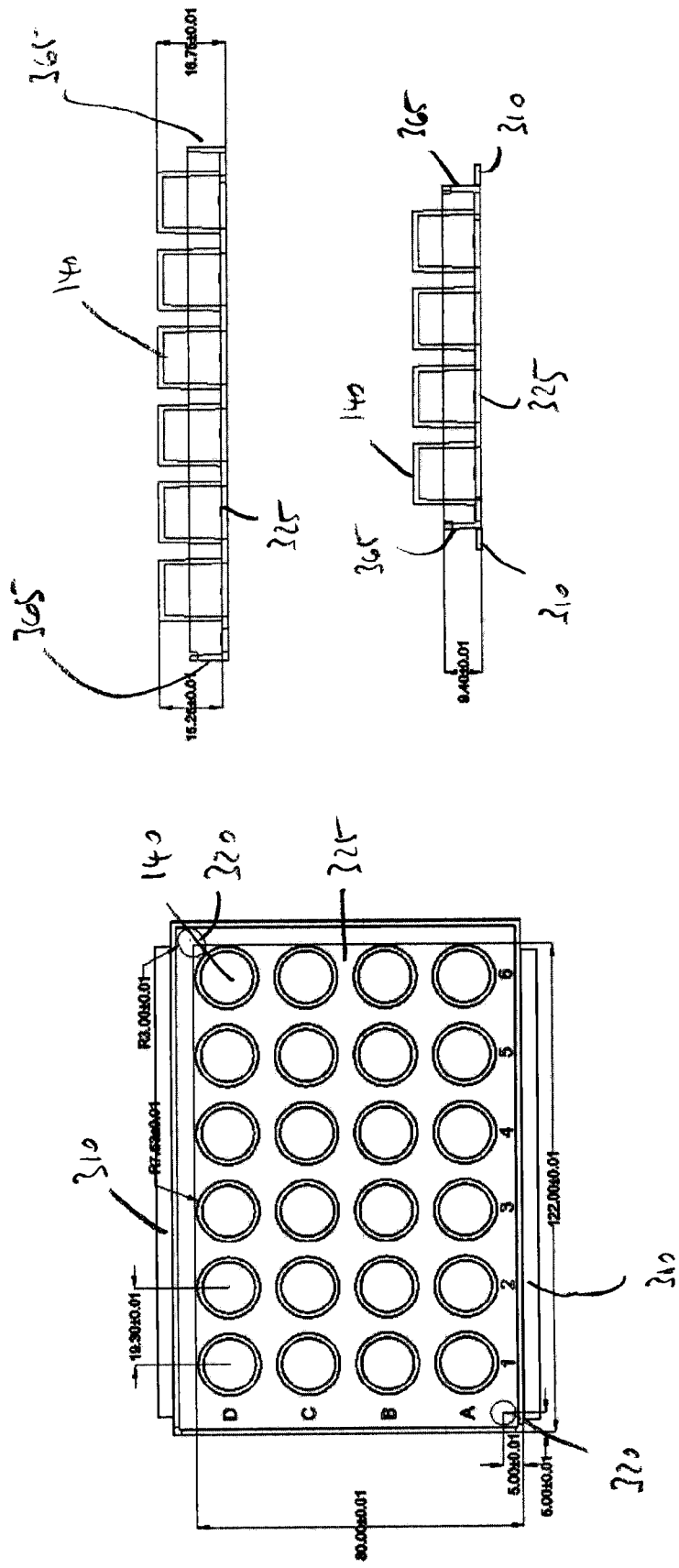
Figure 3D:
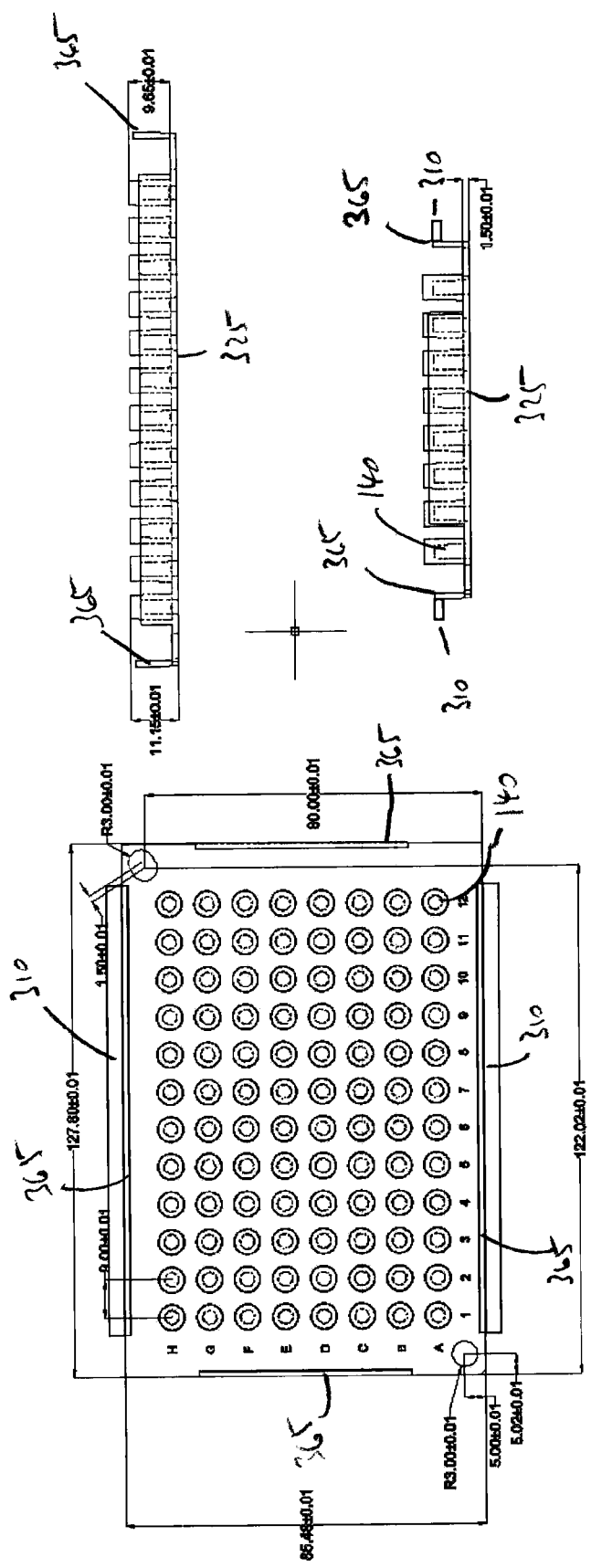

In some embodiments, as illustrated in FIG. 3B, the pillar plate includes a plurality of pillars that extend approximately perpendicular from the pillar plate. In some embodiments, one or more microarrays being affixed to at least one pillar so that each microarray is prevented from being displaced from the at least one pillar when the pillar plate is turned upside down.

In some embodiments, the microarrays are functionalized with distinct analyte-detecting regions or biomolecular probes that are synthesized on a substrate of the microarrays by well-known techniques, e.g., the synthesis described in more detail below. In some embodiments, the microarrays include a wafer. In some embodiments, the microarrays include a support layer. In some embodiments, the support layer includes additional features, for example, micropillars. In some embodiments, one or more microarray is affixed to at least one pillar of the pillar plate so that to prevent displacement of the microarray form the at least one pillar when the pillar plate is turned upside down during assaying biomolecular probes on the microarray. In some embodiments, microarrays are affixed to a top surface of the pillars with an adhesive. In some embodiments, the adhesive is an epoxy, a visible light curable epoxy, an ultraviolet light curable glue, or a heat curable glue epoxy.

In some embodiments, the microarrays disclosed herein include chip arrays. In some embodiments, a chip array is a two-dimensional array of microarrays ("chips") on a plate. In some embodiments, each microarray only includes a single protein or antibody. In other embodiments, each microarray includes a plurality of proteins, antibodies, peptides, oligonucleotides, DNA, RNA, peptide nucleic acid ("PNA"), probe molecules and the like. In some embodiments, the microarray is attached to a cap which attaches to a pillar on a pillar plate.

In one embodiment, microarrays are formed on a silicon wafer, the silicon wafer being the support layer, and then diced into multiple chips of varying dimensions. In some embodiments, each microarray has a dimension of 1 mm by 1 mm up to 2 cm to 2 cm. In some embodiments, the microarrays are formed on a wafer and diced into multiple microarrays that fit onto 24-, 96-, 192-, or 384-pillar plates, or any other custom made plates. In some embodiments, the pillar plate is used for in-vitro diagnostics, such as protein-protein interaction assays or other enzymatic reactions.

In some embodiments, the pillar plates include a plurality of pillars. In some embodiments, number of pillars of the pillar plate is 24, 96,–384, or 1536 pillars. FIG. 3B also illustrates the pillar plate including two protruding edges on opposite sides of the pillar plate. In some embodiments, the pillars have a top surface 340 and bottom surface 345 with the bottom surface mounted to the base region 330. In some embodiments, the protruding edges 310 extend 1 mm from plate support 325. In some embodiments, the protruding edges 310 extend less than 1 mm from the plate support. In some embodiments, the protruding edges 310 extend more than 1 mm from the plate support. In some embodiments, the protruding edges 310 extend a distance from the plate support that falls within a range of 0.5 mm to 5 mm. In some embodiments, the protruding edges extend from the center of the sidewalls 350 of the plate support, as illustrated in FIG. 3B. In embodiments, the protruding edges extend from a region of the sidewalls 340 that is off-center, for example, the lower edges 355 or upper edges 360 of the sidewalls 350.

As illustrated in FIGS. 3C and 3D, in some embodiments, the pillar plates include a periphery wall 365. In some embodiments, the protruding edges 310 extending from the periphery wall 365 instead of the plate support 325, as shown in FIG. 3D. In some embodiments, the protruding edges, the alignment marks, the plate support, the base region, the pillars, the periphery wall are integrally molded features of plate pillar.

Tool Assembly for Assaying Microarrays

Figure 4A:
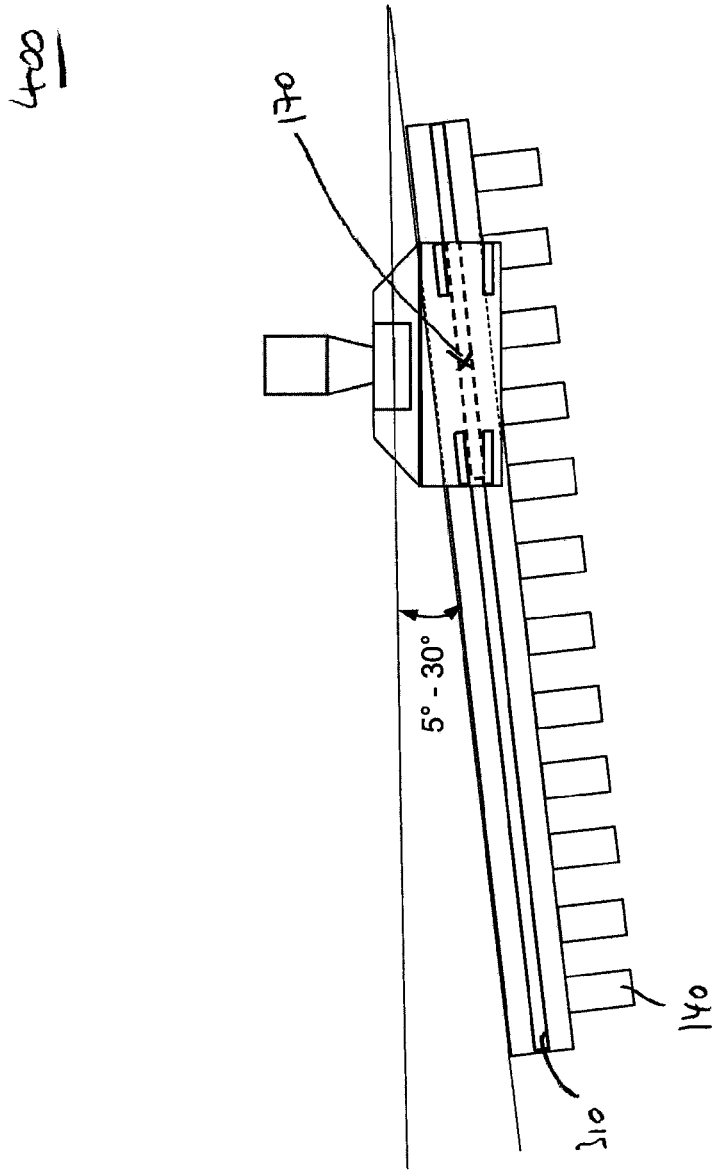
FIGS. 4A and 4B illustrate a side and front view of a tool assembly for assaying microarrays, respectively, according to some embodiments.
Figure 4B:
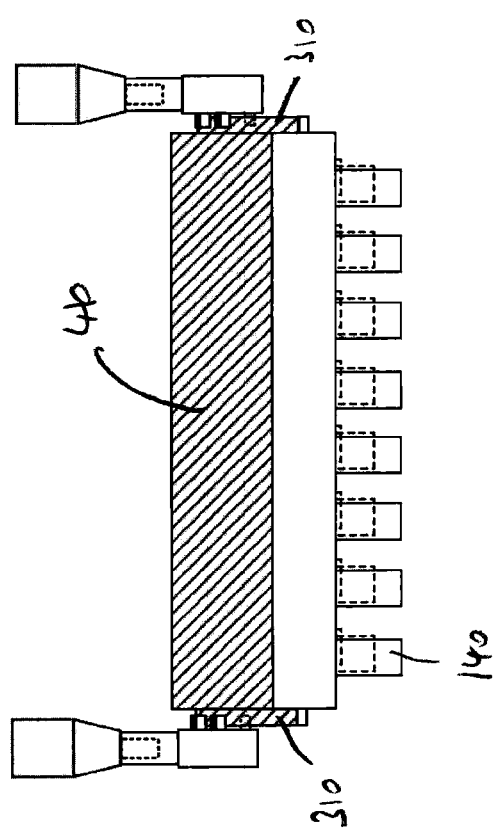

FIGS. 4A and 4B illustrate the side and front view of a tool assembly for assaying microarrays that includes the tool comprising two clamps and the pillar plate, according to some embodiments. In the shown embodiments, each of two protruding edges are both separately interlocked with the two pairs of receiving bars of one of the two clamps as the pillar plate is suspended by the two clamps. Furthermore, in some embodiments, each of two protruding edges are both separately interlocked with the two pairs receiving bars of one of the two clamps as the pillar plate is not freely suspended by the two clamps. The suspended pillar plate is shown at a non-zero tilt angle (5°-30°) in FIGS. 4A and 4B. FIG. 4B illustrates the front view of the tool assembly showing the bottom surface 410 of the pillar plate (shaded area). FIGS. 4A and 4B further illustrate the off-center position 170, at which the grasping portion of the clamps interlock with the protruding edges 310 of the pillar plate.

In some embodiments, the upper receiving bars of the two pairs of receiving bars of each of the two clamps are configured to individually or in combination exert a downward force on the interlocked protruding edges of the pillar plate if the pillar plate is freely suspended by the two clamps. In some embodiments, the lower receiving bars of the second pair of receiving bars are configured to exert an upward force on the interlocked protruding edges of the pillar plate if the pillar plate is freely suspended by the two clamps.

In some embodiments, the two clamps included in the tool assembly are configured to allow the pillar plate to align parallel relative to the plane normal to the tool mount portion if one or more pillars of the pillar plate are immersed beyond a threshold depth within an assay solution in one or more wells of a well plate.

In some embodiments, the lower receiving bars of the pairs of receiving bars of the two clamps are configured to individually or in combination exert an upward force on the interlocked protruding edges of the pillar plate if the pillar plate is not freely suspended by the two clamps. In some embodiments, the upper receiving bars of the second pair of receiving bas of the two clamps are configured to exert a downward force on the interlocked protruding edges of the pillar plate if the pillar plate is not freely suspended by the two clamps In some embodiments of the tool assembly, the number of pillars of the pillar plate is selected from a group consisting of 24, 96, 384, and 1536. In some embodiments of the tool assembly, the pillar plate has an area that is larger than 50 square centimeters.

In some embodiments of the tool assembly, the two clamps each include: (1) a tool mount portion that is configured to engage a lifting mechanism of a plate handling robot for moving a pillar plate comprising microarrays; (2) and a grasping portion that is configured to freely suspend a pillar plate at an inclination of a non-zero tilt angle relative to a plane normal to the tool mount portion.

In some embodiments, the non-zero tilt angle is 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, or 30°. In some embodiments, the non-zero tilt angle is within the range of 5° to 30°, less or equal to 30°, or less or equal to 45°.

In some embodiments, the microarrays are functionalized with distinct analyte-detecting regions or biomolecular probes that are synthesized on a substrate of the microarrays by well-known techniques, e.g., the synthesis described in more detail below. In some embodiments, one or more microarray is affixed to at least one pillar of the pillar plate so that to prevent displacement of the microarray form the at least one pillar when the pillar plate is turned upside down during assaying biomolecular probes on the microarray. In some embodiments, microarrays are affixed to a top surface of the pillars with an adhesive. In some embodiments, the adhesive is an epoxy, a visible light curable epoxy, an ultraviolet light curable glue, or a heat curable glue epoxy.

Microarrays

Also disclosed herein are microarrays. Embodiments of a microarray ("chip") comprise a substrate and features attached to the substrate surface at positionally-defined locations.

In some embodiments, a microarray comprises two-dimensional array, wherein the positionally-defined locations occupy a 2-dimensional plane. For example, each feature can comprise: a collection of peptide chains of determinable sequence and intended length, wherein within an individual feature, the fraction of peptide chains within said collection having the intended length is characterized by an average coupling efficiency for each coupling step of about 98%. In some embodiments, the average coupling efficiency for each coupling step is at least 98.5%. In some embodiments, the average coupling efficiency for each coupling step is at least 99%. In some embodiments, the average coupling efficiency for each coupling step is at least 90, 91, 92, 93, 94, 95, 96, 97, 98, 98.5, 98.6, 98.7, 98.8, 98.9, 99.0, 99.1, 99.2, 99.3, 99.4, 99.5, 99.6, 99.7, 99.8, 99.9, or 100%.

In some embodiments, the features attached to the substrate surface are selected from a group consisting of: proteins, DNA binding sequences, antibodies, peptides, oligonucleotides, nucleic acids, peptide nucleic acids, deoxyribonucleic acids, ribonucleic acids, peptide mimetics, nucleotide mimetics, chelates, biomarkers, and the like.

In some embodiments, the substrate surface of the microarray is functionalized with free amine or free carboxylic acids for polypeptide synthesis. In some embodiments, the free carboxylic acids are activated to bind to amine groups, e.g., during polypeptide synthesis on the surface of the microarray.

In some embodiments, the surface density of features on the microarray is greater than $10/cm^2$, $100/cm^2$, $1,000/cm^2$, $10,000/cm^2$, $100,000/cm^2$, $1,000,000/cm^2$, $10,000,000/cm^2$ or $20,000,000/cm^2$. In some embodiments, the total number of features on the microarray is at least about 100,000, 200,000, 300,000, 400,000, 500,000, 600,000, 700,000, 800, 000, 900,000, 1,000,000, 2,000,000, 3,000,000, 4,000,000, 5,000,000, 6,000,000, 7,000,000, 8,000,000, 10,000,000, 12,000,000, 14,000,000, 16,000,000, or 18,000,000. In other embodiments, the size of the microarray is less than or equal to 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 400, 500, 600, 700, 800, 900, or 1,000 square millimeters.

In some embodiments, a microarray can be a three-dimensional array, e.g., the substrate comprising a porous layer with features attached to the surface of the porous layer. In some embodiments, the surface of a porous layer includes external surfaces and surfaces defining pore volume within the porous layer. In some embodiments, a three-dimensional microarray can include features attached to a surface at positionally-defined locations, said features each comprising: a collection of peptide chains of determinable sequence and intended length. In one embodiment, within an individual feature, the fraction of peptide chains within said collection having the intended length is characterized by an average coupling efficiency for each coupling step of greater than 98%. In some embodiments, the average coupling efficiency for each coupling step is at least 90, 91, 92, 93, 94, 95, 96, 97, 98, 98.5, 98.6, 98.7, 98.8, 98.9, 99.0, 99.1, 99.2, 99.3, 99.4, 99.5, 99.6, 99.7, 99.8, 99.9, or 100%.

In some embodiments, each peptide chain is from 5 to 60 amino acids in length. In some embodiments, each peptide chain is at least 5 amino acids in length. In some embodiments, each peptide chain is at least 5, 10, 15, 20, 25, 30, 35, 40, 45, 50, 55, or 60 amino acids in length. In some embodiments, each peptide chain is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some embodiments, each peptide chain comprises one or more L amino acids. In some embodiments, each peptide chain comprises one or more D amino acids. In some embodiments, each peptide chain comprises one or more naturally occurring amino acids. In some embodiments, each peptide chain comprises one or more synthetic amino acids.

In some embodiments, a microarray can include at least 1,000 different peptide chains attached to the surface. In some embodiments, a microarray can include at least 10,000 different peptide chains attached to the surface. In some embodiments, a microarray can include at least 100, 500, 1000, 2000, 3000, 4000, 5000, 6000, 7000, 8000, 9000, 10,000, or greater than 10,000 different peptide chains attached to the surface (or any integer in between).

In some embodiments, a microarray can include a single protein, peptide chain, or antibody attached to a plurality of different types of linker molecules. In some embodiments a microarray can include at least 2 different types of linker molecules. In some embodiments, a microarray can include at least 2, 3, 4, 5, 6, 7, 8, 9, 10, 15, 20, 25, 30, 40, 50, 75, or greater than 100 different types of linker molecules attached to the substrate.

In some embodiments, each of the positionally-defined locations is at a different, known location that is physically separated from each of the other positionally-defined locations. In some embodiments, each of the positionally-defined locations is a positionally-distinguishable location. In some embodiments, each determinable sequence is a known sequence. In some embodiments, each determinable sequence is a distinct sequence.

In some embodiments, the features are covalently attached to the surface. In some embodiments, said peptide chains are attached to the surface through a linker molecule or a coupling molecule.

In some embodiments, the features comprise a plurality of distinct, nested, overlapping peptide chains comprising subsequences derived from a source protein having a known sequence. In some embodiments, each peptide chain in the plurality is substantially the same length. In some embodiments, each peptide chain in the plurality is the same length. In some embodiments, each peptide chain in the plurality is at least 5 amino acids in length. In some embodiments, each peptide chain in the plurality is at least 5, 10, 15, 20, 25, 30, 35, 40, 45, 50, 55, or 60 amino acids in length. In some embodiments, each peptide chain in the plurality is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some embodiments, at least one peptide chain in the plurality is at least 5 amino acids in length. In some embodiments, at least one peptide chain in the plurality is at least 5, 10, 15, 20, 25, 30, 35, 40, 45, 50, 55, or 60 amino acids in length. In some embodiments, at least one peptide chain in the plurality is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some embodiments, each polypeptide in a feature is substantially the same length. In some embodiments, each polypeptide in a feature is the same length. In some embodiments, the features comprise a plurality of peptide chains each having a random, determinable sequence of amino acids.

Methods

Methods of Using the Tool Assembly for Assaying Microarrays

Also disclosed herein are methods of using substrates, formulations, and/or microarrays. Uses of the microarrays disclosed herein can include research applications, therapeutic purposes, medical diagnostics, and/or stratifying one or more patients.

Figure 5:
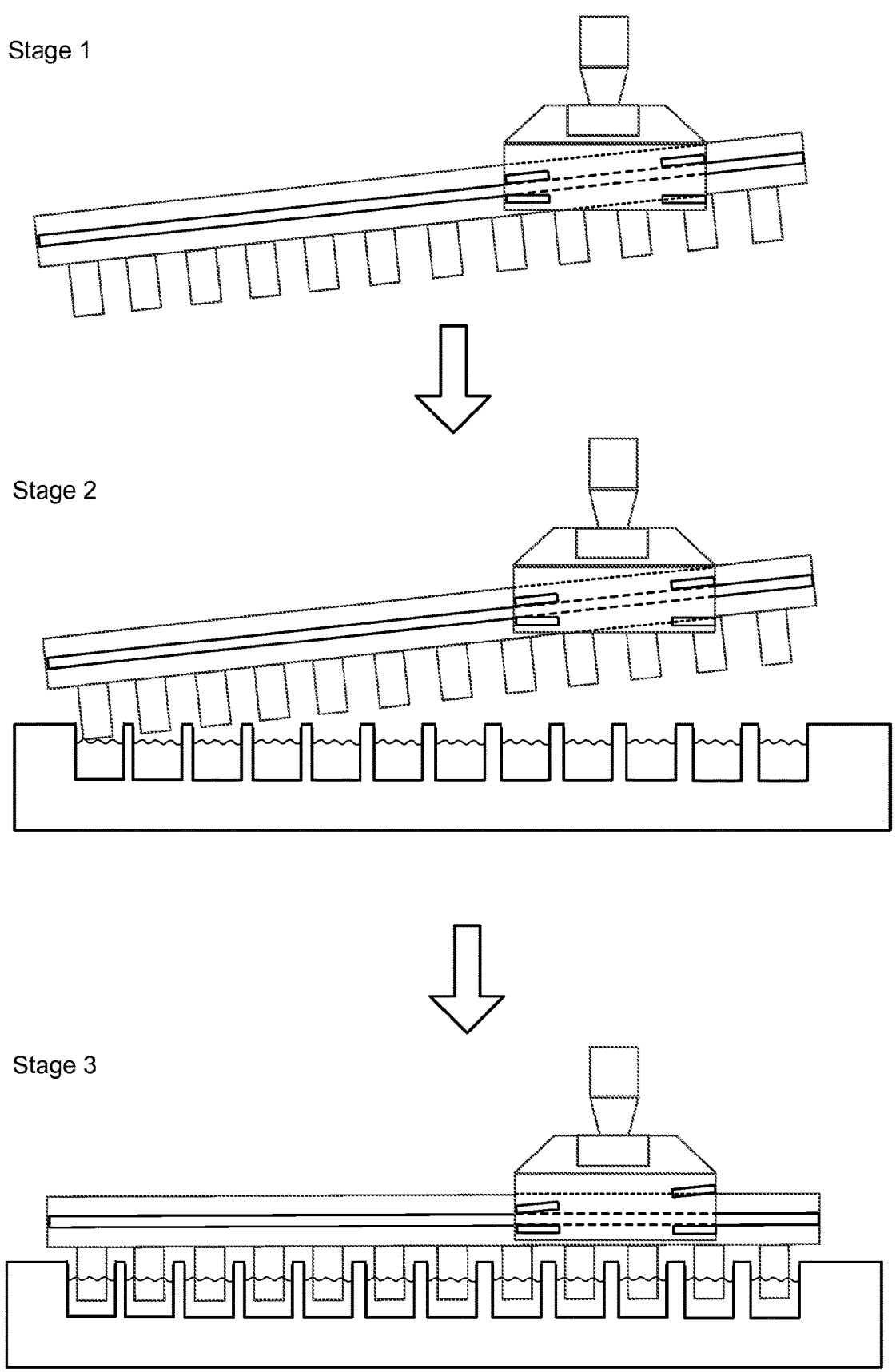
FIG. 5 illustrate a tool assembly for assaying microarrays at different stages of performing steps in assaying microarrays, according to some embodiments.

FIG. 5 illustrate a tool assembly for assaying microarrays at different stages of performing steps in assaying microarrays, according to some embodiments. The method of using a tool assembly for assaying microarrays that reduces the likelihood of air bubbles being trapped by the microarrays includes the following steps. A tool assembly as described is provided first. In addition, a well plate that includes a plurality of wells is provided. Each well is capable of receiving one pillar of the pillar plate, when the pillar plate is inclined at the non-zero tilt angle relative to the plane normal to the tool mount portion of the clamps and the microarrays are contacted with an assay solution in one or more wells of the well plate. In some embodiments, the wells are of cylindrical or rectangular shape. To allow the wells to receive the pillars, the diameter of the wells exceeds the cross-sectional diameter of the pillars as measured perpendicular relative to the tool mount portion of the clamps.

Next, the pillar plate of the tool assembly is freely suspended inclined at the non-zero tilt angle relative to the plane normal to the tool mount portion of the clamps. This step includes interlocking the protruding edges of the pillar plate with the grasping portions of the clamps while the pillar plate is turned upside down and the tool mount portion of the clamps are engaged with a lifting mechanism of a plate handling robot. The one or more microarrays affixed to the at least one pillar of the pillar plate are assayed by moving the freely suspended pillar plate towards the well plate and contacting the one or more microarray with an assay solution in the wells.

The stages shown in FIG. 5 include the tool assembly in a first stage of the freely suspended and inverted pillar plate. The second stage shows the tool assembly with the one of the pillars of the pillar plate contacting the assay solution in one of the wells. In both stages, the pillar plate is suspended at a non-zero tilt angle. The third stage shows the pillars of pillar plate immersed in the assay solution. The solution buoys the pillar plate, counteracting the gravitational forces acting on the pillar plate. In the third stage, the pillar plate is aligned parallel relative to the plane normal to the tool mount portion. In this stage, the lower receiving bars of the two pairs of each clamps still provide support for the pillar plate, preventing the pillars from moving even further downwards into the wells.

Any of the microarrays described herein can be used as a research tool or in a research application. In one embodiment, microarrays can be used for high throughput screening assays. For example, enzyme substrates (i.e., peptides on a peptide microarray described herein) can be tested by subjecting the microarray to an enzyme and identifying the presence or absence of enzyme substrate(s) on the microarray, e.g., by detecting at least one change among the features of the microarray.

Microarrays can also be used in screening assays for ligand binding, to determine substrate specificity, or for the identification of peptides that inhibit or activate proteins. Labeling techniques, protease assays, as well as binding assays useful for carrying out these methodologies are generally well-known to one of skill in the art.

In some embodiments, a microarray can be used to represent a known protein sequence as a sequence of overlapping peptides. For example, the amino acid sequence of a known protein is divided into overlapping sequence segments of any length and of any suitable overlapping frame, and peptides corresponding to the respective sequence segments are in-situ synthesized as disclosed herein. The individual peptide segments so synthesized can be arranged starting from the amino terminus of the known protein.

In some embodiments, a microarray is used in a method wherein the antigenic representation of the microarray includes at least one region where the whole antigen sequence of a known protein is spanned via epitope sliding; the immunoactive regions of the antigen are determined by contacting one or more clinical samples on the array or a plurality of different microarrays, and the set of peptide sequences required to represent the known protein antigen are reduced.

In some embodiments, a sample is applied to a microarray having a plurality of random peptides. The random peptides can be screened and BLASTed to determine homologous domains with, e.g., a 90% or more identity to a given antigenic sequence. In some embodiment, the whole antigenic sequence can then be synthesized and used to identify potential markers and/or causes of a disease of interest.

In some embodiments, a microarray is used for high throughput screening of one or more genetic factors. Proteins associated with a gene can be a potential antigen and antibodies against these proteins can be used to estimate the relation between gene and a disease.

In another example, a microarray can be used to identify one or more biomarkers. Biomarkers can be used for the diagnosis, prognosis, treatment, and management of diseases. Biomarkers may be expressed, or absent, or at a different level in an individual, depending on the disease condition, stage of the disease, and response to disease treatment. Biomarkers can be, e.g., DNA, RNA, proteins (e.g., enzymes such as kinases), sugars, salts, fats, lipids, or ions.

Microarrays can also be used for therapeutic purposes, e.g., identifying one or more bioactive agents. A method for identifying a bioactive agent can comprise applying a plurality of test compounds to a microarray and identifying at least one test compound as a bioactive agent. The test compounds can be small molecules, aptamers, oligonucleotides, chemicals, natural extracts, peptides, proteins, fragment of antibodies, antibody like molecules or antibodies. The bioactive agent can be a therapeutic agent or modifier of therapeutic targets. Therapeutic targets can include phosphatases, proteases, ligases, signal transduction molecules, transcription factors, protein transporters, protein sorters, cell surface receptors, secreted factors, and cytoskeleton proteins.

In another embodiment, a microarray can be used to identify drug candidates for therapeutic use. For example, when one or more epitopes for specific antibodies are determined by an assay (e.g., a binding assay such as an ELISA), the epitopes can be used to develop a drug (e.g., a monoclonal neutralizing antibody) to target antibodies in disease.

In one embodiment, also provided are microarrays for use in medical diagnostics. An array can be used to determine a response to administration of drugs or vaccines. For example, an individual's response to a vaccine can be determined by detecting the antibody level of the individual by using a microarray with peptides representing epitopes recognized by the antibodies produced by the induced immune response. Another diagnostic use is to test an individual for the presence of biomarkers, wherein samples are taken from a subject and the sample is tested for the presence of one or more biomarkers.

Microarrays can also be used to stratify patient populations based upon the presence or absence of a biomarker that indicates the likelihood a subject will respond to a therapeutic treatment. The microarrays can be used to identify known biomarkers to determine the appropriate treatment group. For example, a sample from a subject with a condition can be applied to a microarray. Binding to the microarray may indicate the presence of a biomarker for a condition. Previous studies may indicate that the biomarker is associated with a positive outcome following a treatment, whereas absence of the biomarker is associated with a negative or neutral outcome following a treatment. Because the patient has the biomarker, a health care professional may stratify the patient into a group that receives the treatment.

In some embodiments, a method of detecting the presence or absence of a molecule of interest (e.g., a protein, an antibody, or any other ligand) in a sample can include obtaining a microarray disclosed herein and contacted with a sample suspected of comprising the molecule of interest; and determining whether the molecule of interest is present in the sample by detecting the presence or absence of binding to one or more features of the microarray.

In some embodiments, a molecule of interest can be detected within a sample that has a volume that is less than or equal to 100, 50, 10, 5, 1.5, or 1 µL. In some embodiments, the elapsed time from the sample contacting to detection of a molecule of interest is less than 40, 30, 20, 19, 18, 17, 16, 15, 14, 13, 12, 11, 10, 9, 8, 7, 6, 5, 4, 3, 2, or 1 minutes. In some embodiment, a molecule of interest can be detected at a concentration in the contacted sample that falls within the range of about 1 pg/ml to 1,000 µg/ml.

In some embodiments, the protein of interest may be obtained from a bodily fluid, such as amniotic fluid, aqueous humour, vitreous humour, bile, blood serum, breast milk, cerebrospinal fluid, cerumen, chyle, endolymph, perilymph, feces, female ejaculate, gastric acid, gastric juice, lymph, mucus, peritoneal fluid, pleural fluid, pus, saliva, sebum, semen, sweat, synovial fluid, tears, vaginal secretion, vomit, or urine.

In some embodiments, a method of identifying a vaccine candidate can include obtaining a microarray disclosed herein contacted with a sample derived from a subject previously administered the vaccine candidate, wherein the sample comprises a plurality of antibodies; and determining the binding specificity of the plurality of antibodies to one or more features of the microarray. In some embodiments, the features comprise a plurality of distinct, nested, overlapping peptide chains comprising subsequences derived from a source protein having a known sequence.

Methods of Manufacturing Microarrays

Also disclosed herein are methods for manufacturing microarrays. In some embodiments, the microarrays disclosed herein can be synthesized in situ on a surface, e.g., the substrate disclosed herein. In some instances, the microarrays are made using photolithography. For example, the substrate is contacted with a photoactive coupling solution. Masks can be used to control radiation or light exposure to specific locations on a surface provided with free linker molecules or free coupling molecules having protecting groups. In the exposed locations, the protecting groups are removed, resulting in one or more newly exposed reactive moieties on the coupling molecule or linker molecule. The desired linker or coupling molecule is then coupled to the unprotected attached molecules, e.g., at the carboxylic acid group. The process can be repeated to synthesize a large number of features in specific or positionally-defined locations on a surface (see, for example, U.S. Pat. No. 5,143,854 to Pirrung et al., U.S. Patent Application Publication No. 2007/0154946 (filed on Dec. 29, 2005), 2007/0122841 (filed on Nov. 30, 2005), 2007/0122842 (filed on Mar. 30, 2006), 2008/0108149 (filed on Oct. 23, 2006), and 2010/0093554 (filed on Jun. 2, 2008), each of which is herein incorporated by reference).

In some embodiments, a method of producing a three-dimensional microarray of features, can include obtaining a porous layer attached to a surface; and attaching the features to the porous layer, said features each comprising a collection of peptide chains of determinable sequence and intended length, wherein within an individual feature, the fraction of peptide chains within said collection having the intended length is characterized by an average coupling efficiency for each coupling step of at least about 98%. In some embodiments, the features are attached to the surface using a photoactive coupling formulation, comprising a photoactive compound, a coupling molecule, a coupling reagent, a polymer, and a solvent. In some embodiments, the features are attached to the surface using a photoactive coupling formulation disclosed herein. In some embodiments, the photoactive coupling formulation is stripped away using water.

In one embodiment, described herein is a process of manufacturing an microarray. A surface comprising attached carboxylic acid groups is provided. The surface is contacted with a photoactive coupling solution comprising a photoactive compound, a coupling molecule, a coupling reagent, a polymer, and a solvent. The surface is exposed to ultraviolet light in a deep ultra violet scanner tool according to a pattern defined by a photomask, wherein the locations exposed to ultraviolet light undergo photo base generation due to the presence of a photobase generator in the photoactive coupling solution. The expose energy can be from 1 mJ/cm$^2$ to 100 mJ/cm$^2$ in order to produce enough photobase.

The surface is post baked upon exposure in a post exposure bake module. Post exposure bake acts as a chemical amplification step. The baking step amplifies the initially generated photobase and also enhances the rate of diffusion to the substrate. The post bake temperature can vary between 75° Celsius to 115° Celsius, depending on the thickness of the porous surface, for at least 60 seconds and not usually exceeding 120 seconds. The free carboxylic acid group is coupled to the deprotected amine group of a free peptide or polypeptide, resulting in coupling of the free peptide or polypeptide to the carboxylic acid group attached to the surface. This surface may be a porous surface. The synthesis of peptides coupled to a carboxylic acid group attached to the surface occurs in an N→C synthesis orientation, with the amine group of free peptides attaching to carboxylic acid groups bound to the surface of the substrate. Alternatively, a diamine linker may be attached to a free carboxylic acid group to orient synthesis in a C→N direction, with the carboxylic acid group of free peptides attaching to amine groups bound to the surface of the substrate.

The photoactive coupling solution can now be stripped away. In some embodiments, provided herein is a method of stripping the photoresist completely with deionized (DI) water. This process is accomplished in a developer module. The wafer is spun on a vacuum chuck for, e.g., 60 seconds to 90 seconds and deionized water is dispensed through a nozzle for about 30 seconds.

The photoactive coupling formulation may be applied to the surface in a coupling spin module. A coupling spin module can typically have 20 nozzles or more to feed the photoactive coupling formulation. These nozzles can be made to dispense the photoactive coupling formulation by means of pressurizing the cylinders that hold these solutions or by a pump that dispenses the required amount. In some embodiments, the pump is employed to dispense 5-8 cc of the photoactive coupling formulation onto the substrate. The substrate is spun on a vacuum chuck for 15-30 seconds and the photoactive coupling formulation is dispensed. The spin speed can be set to 2000 rpm to 2500 rpm.

Optionally, a cap film solution coat is applied on the surface to prevent the non-reacted amino groups on the substrate from reacting with the next coupling molecule. The cap film coat solution can be prepared as follows: a solvent, a polymer, and a coupling molecule. The solvent that can be used can be an organic solvent like N-methyl pyrrolidone, dimethyl formamide, or combinations thereof. The capping molecule is typically acetic anhydride and the polymer can be polyvinyl pyrrolidone, polyvinyl alcohol, polymethyl methacrylate, poly-(methyl-isopropenyl)-ketone, or poly-(2-methyl-pentene-1-sulfone). In some embodiments, the capping molecule is ethanolamine.

This process is done in a capping spin module. A capping spin module can include one nozzle that can be made to dispense the cap film coat solution onto the substrate. This solution can be dispensed through pressurizing the cylinder that stores the cap film coat solution or through a pump that precisely dispenses the required amount. In some embodiments, a pump is used to dispense around 5-8 cc of the cap coat solution onto the substrate. The substrate is spun on a vacuum chuck for 15-30 seconds and the coupling formulation is dispensed. The spin speed can be set to 2000 to 2500 rpm.

The substrates with the capping solution are baked in a cap bake module. A capping bake module is a hot plate set up specifically to receive wafers just after the capping film coat is applied. In some embodiments, provided herein is a method of baking the spin coated capping coat solution in a hot plate to accelerate the capping reaction significantly. Hot plate baking generally reduces the capping time for amino acids to less than two minutes.

The byproducts of the capping reaction are stripped in a stripper module. A stripper module can include several nozzles, typically up to 10, set up to dispense organic solvents such as acetone, isopropyl alcohol, N-methyl pyrrolidone, dimethyl formamide, DI water, etc. In some embodiments, the nozzles can be designated for acetone followed by isopropyl alcohol to be dispensed onto the spinning wafer. The spin speed is set to be 2000 to 2500 rpm for around 20 seconds.

This entire cycle can be repeated as desired with different coupling molecules each time to obtain a desired sequence.

In some embodiments, a microarray comprising a surface of free carboxylic acids is used to synthesize polypeptides in an N→C orientation. In one embodiment, the carboxylic acids on the surface of the substrate are activated (e.g., converted to a carbonyl) to allow them to bind to free amine groups on an amino acid. In one embodiment, activation of carboxylic acids on the group of the surface can be done by addition of a solution comprising a carbodiimide or succinimide to the surface of the microarray. In some embodiments, carboxylic acids can be activated by addition of a solution comprising 1-ethyl-3-(3-dimethyl-aminopropyl)-carbodiimide (EDC), N-hydroxysuccinimide (NHS), 1,3-diisopropyl-carbodiimide (DIC), hydroxybenzotriazole (HOBt), O-(7-azabenzotriazol-1-yl)-N,N,N',N'-tetramethyluronium hexafluorophosphate (HATU), benzotriazol-1-yl-oxytripyrrolidinophosphonium hexafluorophosphate (PyBOP), or N,N-diisopropylethylamine (DIEA) to the surface of the microarray. The activation solution is washed away and the surface of the microarray is prepared for addition of an amino acid layer (i.e., one amino acid at each activated carboxylic acid group). Carboxylic acid groups remain activated for up to 2, 3, 4, 5, 6, 7, 8, 9, or 10 hours.

Addition of a solution comprising an amino acid with a free amine group to the activated carboxylic acid surface of the microarray results in binding of a single amino acid to each carboxylic acid group. In some embodiments, the amino acid comprises an amino acid with protected amine groups. Using a photosensitive chemical reaction, the protecting group can be removed from the amine group of selected amino acids at site-specific locations using a reticle. For example, Fmoc-protected amino acids are mixed in a solution comprising a photobase. Upon exposure of the solution on the microarray to a specific frequency of light at site-specific locations, the photobase will release a base which will deprotect the amino acid, resulting in coupling of the amino acid to the activated carboxylic acid group on the surface of the microarray. Another method of generating a base is through the use of a photoacid generator. In some embodiments, the photoacid generator is N-boc-piperidine or 1-boc-4-piperazine.

After a completed layer of amino acids is coupled, remaining uncoupled activated carboxylic acids are capped to prevent nonspecific binding of amino acids on subsequent synthesis steps. The steps of activation, addition of an amino acid layer, and capping are repeated as necessary to synthesize the desired polypeptides at specific locations on the microarray.

In one embodiment, peptides synthesized in the N→C terminus direction can be capped with a diamine molecule to enhance binding properties of selected polypeptide sequences to a biological molecule, e.g., an antibody. In other embodiments, peptides synthesized in the C→N direction can be capped with a dicarboxylic acid molecule to enhance binding properties of selected sequences to a biological molecule.

While synthesizing polypeptides in parallel on the surface of a microarray, the method described herein ensures complete activation of carboxylic acid on the surface of the microarray. Due to stability of the activated ester for an extended period of time, 2, 3, 4, 5, 6, 7, 8, 9, 10, 11, 12, 13, 14, 15, 16, 17, 18, 19, 20, 21, 22, 23, 24, 25 or more coupling cycles may be completed after a single activation step (e.g., to couple an entire layer of 2-25 or more different amino acids at different locations on the microarray). As the coupling occurs during hard bake (heating in a hot plate at 85-90° Celsius for 90 seconds immediately after coating) and due to the presence of excess amino acid in the solution, complete 100% deprotection of Fmoc-protected amino acid may not be required for significantly high coupling yields. After addition of all amino acids and capping, all free activated carboxylic acids are either coupled or capped, thus resulting in high efficiency and accuracy of polypeptide synthesis.

In some embodiments, other methods are used to functionalize microarrays, which are described in International Patent Application Nos. PCT/US2013/025190, PCT/US2013/062773, PCT/US2013/070207, PCT/US2014/016737, PCT/US2015/017173, and PCT/US2015/049528, the contents of which are incorporated hereby by reference.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A tool for assaying microarrays that reduces the likelihood of air bubbles being trapped by the microarrays, comprising:
two clamps, each of the two clamps comprising:
a tool mount portion, the tool mount portion configured to engage a lifting mechanism of a plate handling robot configured to move a pillar plate comprising microarrays, and
a grasping portion, the grasping portion configured to freely suspend the pillar plate at an inclination of a non-zero tilt angle relative to a plane normal to the tool mount portion,
wherein the grasping portion of each clamp comprises two pairs of receiving bars, each receiving bar pair comprising an upper receiving bar and a lower receiving bar, the receiving bars of the first pair being separated at a first vertical width, the receiving bars of the second pair being separated at a second vertical width, and the first vertical width exceeding the second vertical width by a pre-defined threshold distance whereby the pillar plate assumes the non-zero tilt angle if the pillar plate is freely suspended by the two clamps.

2. The tool of claim 1, wherein the upper receiving bars of the two pairs of receiving bars are aligned at the non-zero tilted angle and the lower receiving bars are aligned parallel relative to a plane normal to the tool mount portion.

3. The tool of claim 1, wherein the grasping portions of the two clamps are configured to allow a planar surface of the pillar plate to align parallel relative to the plane normal to the tool mount portion if the pillar plate is not freely suspended by the two clamps and is instead buoyant by an assay solution in the one or more wells of a well plate.

4. The tool of claim 1, wherein the non-zero tilt angle is within the range of 5° to 30°.

5. The tool of claim 1, wherein the non-zero tilt angle is 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, or 30°.

6. The tool of claim 1, wherein the non-zero tilt angle is less or equal to 30° and greater than zero degrees.

7. The tool of claim 1, wherein the non-zero tilt angle is less or equal to 45° and greater than zero degrees.

8. A tool assembly for assaying microarrays that reduces the likelihood of air bubbles being trapped by the microarrays, comprising:
a tool of claim 1; and
a pillar plate comprising a plurality of pillars that extend approximately perpendicular from the pillar plate, one or more microarrays being affixed to at least one pillar so that each microarray is prevented from being displaced from the at least one pillar when the pillar plate is turned upside down, and the pillar plate further comprising two protruding edges on opposite sides of the pillar plate, wherein the protruding edges are configured to engage with the grasping portions of the clamps to suspend the pillar plate.

9. The tool assembly of claim 8, wherein each of two protruding edges are both separately interlocked with the two pairs of receiving bars of one of the two clamps when the pillar plate is suspended by the two clamps.

10. The tool assembly of claim 9, wherein the upper receiving bars of the two pairs of receiving bars of each of the two clamps are configured to individually or in combination exert a downward force on the interlocked protruding edges of the pillar plate when the pillar plate is freely suspended by the two clamps.

11. The tool assembly of claim 9, wherein the lower receiving bars of the second pair of receiving bars are configured to exert an upward force on the interlocked protruding edges of the pillar plate when the pillar plate is freely suspended by the two clamps.

12. The tool assembly of claim 8, wherein each of two protruding edges are both separately interlocked with the two pairs of receiving bars of one of the two clamps when the pillar plate is not freely suspended by the two clamps.

13. The tool assembly of claim 8, wherein the two clamps are configured to allow the pillar plate to align parallel relative to the plane normal to the tool mount portion when one or more pillars of the pillar plate are immersed beyond a threshold depth within an assay solution in one or more wells of a well plate.

14. The tool assembly of claim 9, wherein the lower receiving bars of the pairs of receiving bars of the two clamps are configured to individually or in combination exert an upward force on the interlocked protruding edges of the pillar plate when the pillar plate is not freely suspended by the two clamps.

15. The tool assembly of claim 9, wherein the upper receiving bars of the second pair of receiving bas of the two clamps are configured to exert a downward force on the interlocked protruding edges of the pillar plate when the pillar plate is not freely suspended by the two clamps.

16. The tool assembly of claim 8, wherein the number of pillars of the pillar plate is selected from a group consisting of 24, 96,384, and 1536.

17. The tool assembly of claim 8, wherein the non-zero tilt angle is within the range of 5° to 30°.

18. The tool assembly of claim 8, wherein the non-zero tilt angle is 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, or 30°.

19. The tool assembly of claim 8, wherein the non-zero tilt angle is less or equal to 30° and greater than zero degrees.

20. The tool assembly of claim 8, wherein the non-zero tilt angle is less or equal to 45° and greater than zero degrees.

21. The tool assembly of claim 8, wherein the pillar plate has an area that is larger than 50 square centimeters.

22. The tool assembly of claim 8, wherein the tool assembly comprises an adhesive on a top surface of the pillars and said microarrays are affixed to the top surface of the pillars by the adhesive.

23. The tool assembly of claim 22, wherein said adhesive is selected from the group consisting of an epoxy, a visible light curable epoxy, an ultraviolet light curable glue, and a heat curable glue epoxy.

24. A method of using a tool assembly for assaying microarrays that reduces the likelihood of air bubbles being trapped by the microarrays, comprising:
  providing a tool assembly; wherein said tool assembly comprises a tool and a pillar plate; and
  wherein said tool comprises two clamps, and wherein each of the two clamps comprises:
    (1) a tool mount portion, the tool mount portion configured to engage a lifting mechanism of a plate handling robot for moving the pillar plate, and
    (2) a grasping portion, the grasping portion configured to freely suspend the pillar plate at an inclination of a non-zero tilt angle relative to a plane normal to the tool mount portion, wherein the grasping portion of each clamp comprises two pairs of receiving bars, each receiving bar pair comprising an upper receiving bar and a lower receiving bar, the receiving bars of the first pair being separated at a first vertical width, the receiving bars of the second pair being separated at a second vertical width, and the first vertical width exceeding the second vertical width by a pre-defined threshold distance whereby the pillar plate assumes the non-zero tilt angle if the pillar plate is freely suspended by the two clamps; and
  wherein said pillar plate comprises a plurality of pillars that extend approximately perpendicular from the pillar plate, wherein one or more microarrays are affixed to at least one pillar so that each microarray is prevented from being displaced from the at least one pillar when the pillar plate is turned upside down, and the pillar plate further comprising two protruding edges on opposite side of the pillar plate, wherein the protruding edges are configured to engage with the grasping portions of the clamps to suspend the pillar plate;
  providing a well plate comprising a plurality of wells, each well capable of receiving one pillar of the pillar plate, when the pillar plate is inclined at the non-zero tilt angle relative to the plane normal to the tool mount portion of the clamps and the microarrays are contacted with an assay solution in one or more wells of the well plate; freely suspending the pillar plate of the tool assembly inclined at the non-zero tilt angle relative to the plane normal to the tool mount portion of the clamps, the freely suspending comprising interlocking the protruding edges of the pillar plate with the grasping portions of the clamps while the pillar plate is turned upside down and the tool mount portion of the clamps are engaged with a lifting mechanism of a plate handling robot; and assaying the one or more microarrays affixed to the at least one pillar of the pillar plate by moving the freely suspended pillar plate towards the well plate and contacting the one or more microarray with an assay solution in the wells.

\* \* \* \* \*

UNITED STATES PATENT AND TRADEMARK OFFICE
CERTIFICATE OF CORRECTION

| | |
|---|---|
| PATENT NO. | : 11,033,904 B2 |
| APPLICATION NO. | : 15/771381 |
| DATED | : June 15, 2021 |
| INVENTOR(S) | : John J. Rajasekaran et al. |

It is certified that error appears in the above-identified patent and that said Letters Patent is hereby corrected as shown below:

In the Claims

In Column 23, Claim 15, Line 5, replace "bas" with --bars--.

Signed and Sealed this
Seventeenth Day of January, 2023

*Katherine Kelly Vidal*

Katherine Kelly Vidal
*Director of the United States Patent and Trademark Office*